United States Patent
Pigott

(10) Patent No.: US 10,603,069 B2
(45) Date of Patent: Mar. 31, 2020

(54) INTRAVASCULAR CATHETER BALLOON DEVICE HAVING A TOOL FOR ATHERECTOMY OR AN INCISING PORTION FOR ATHEROMATOUS PLAQUE SCORING

(71) Applicant: John P. Pigott, Sylvania, OH (US)

(72) Inventor: John P. Pigott, Sylvania, OH (US)

(*) Notice: Subject to any disclaimer, the term of this patent is extended or adjusted under 35 U.S.C. 154(b) by 694 days.

(21) Appl. No.: 14/991,493

(22) Filed: Jan. 8, 2016

(65) Prior Publication Data
US 2016/0199091 A1    Jul. 14, 2016

Related U.S. Application Data

(60) Provisional application No. 62/102,755, filed on Jan. 13, 2015.

(51) Int. Cl.
| | | |
|---|---|---|
| A61B 17/3207 | (2006.01) | |
| A61B 17/32 | (2006.01) | |
| A61B 17/22 | (2006.01) | |
| A61M 25/10 | (2013.01) | |
| A61B 17/00 | (2006.01) | |

(52) U.S. Cl.
CPC ............ *A61B 17/320725* (2013.01); *A61B 2017/00893* (2013.01); *A61B 2017/22061* (2013.01); *A61B 2017/320004* (2013.01); *A61B 2017/320008* (2013.01); *A61M 2025/109* (2013.01)

(58) Field of Classification Search
CPC .. A61B 17/320725; A61B 2017/00893; A61B 2017/22061; A61B 2017/320004; A61B 2017/320008; A61M 2025/109
See application file for complete search history.

(56) References Cited

U.S. PATENT DOCUMENTS

| | | |
|---|---|---|
| 2,655,154 A | 10/1953 | Richter |
| 3,557,794 A | 1/1971 | Van Patten |
| 3,704,711 A | 12/1972 | Park |
| 4,273,128 A | 6/1981 | Lary |
| 4,292,974 A | 10/1981 | Fogarty et al. |

(Continued)

FOREIGN PATENT DOCUMENTS

| | | |
|---|---|---|
| EP | 0727194 A1 | 8/1996 |
| WO | 8102109 A1 | 8/1981 |

(Continued)

OTHER PUBLICATIONS

Cardiovascular Systems Inc., Diamondback 360 Coronary Orbital Atherectomy System, http://www.csi360.com/products/coronary-diamondback-360-coronary-orbital-atherectomy-system-crowns/, 2016.

(Continued)

*Primary Examiner* — Nathan R Price
*Assistant Examiner* — John A Doubrava
(74) *Attorney, Agent, or Firm* — Standley Law Group LLP

(57) ABSTRACT

An apparatus and method is disclosed for an intravascular balloon device having a balloon and a handle where a catheter tube extends between the two. The handle assembly includes an inflation device in fluid communication with the balloon. A medical tool is provided on the outer surface of the balloon for the treatment of intravascular conditions. The medical tool may be configured to score or remove atherosclerotic material.

5 Claims, 4 Drawing Sheets

(56) References Cited

U.S. PATENT DOCUMENTS

| | | | |
|---|---|---|---|
| 4,654,027 A * | 3/1987 | Dragan | A61M 25/10185 |
| | | | 137/614.2 |
| 5,030,201 A | 7/1991 | Palestrant | |
| 5,074,871 A | 12/1991 | Groshong | |
| 5,100,425 A | 3/1992 | Fischell et al. | |
| 5,154,724 A | 10/1992 | Andrews | |
| 5,156,610 A | 10/1992 | Reger | |
| 5,178,625 A | 1/1993 | Groshong | |
| 5,211,651 A | 5/1993 | Reger et al. | |
| 5,224,945 A | 7/1993 | Pannek, Jr. | |
| 5,224,619 A | 9/1993 | Burnham | |
| 5,246,421 A | 9/1993 | Saab | |
| 5,250,060 A | 10/1993 | Carbo et al. | |
| 5,282,484 A | 2/1994 | Reger | |
| 5,312,427 A | 5/1994 | Shturman | |
| 5,318,576 A | 6/1994 | Plassche, Jr. et al. | |
| 5,514,093 A | 5/1996 | Ellis et al. | |
| 5,591,194 A | 1/1997 | Berthiaume | |
| 5,658,309 A | 8/1997 | Berthiaume et al. | |
| 5,665,098 A | 9/1997 | Kelly et al. | |
| 5,676,654 A | 10/1997 | Ellis et al. | |
| 5,697,944 A | 12/1997 | Lary | |
| 5,697,948 A | 12/1997 | Marin et al. | |
| 5,728,067 A | 3/1998 | Enger | |
| 5,728,123 A | 3/1998 | Lemelson et al. | |
| 5,733,296 A | 3/1998 | Rogers et al. | |
| 5,792,158 A * | 8/1998 | Lary | A61B 17/320725 |
| | | | 604/22 |
| 5,800,450 A | 9/1998 | Lary et al. | |
| 5,836,868 A | 11/1998 | Ressemann et al. | |
| 5,876,448 A | 3/1999 | Thompson et al. | |
| 5,961,536 A | 10/1999 | Mickley et al. | |
| 5,968,064 A | 10/1999 | Selmon et al. | |
| 6,071,287 A | 6/2000 | Verbeek | |
| 6,120,515 A | 9/2000 | Rogers et al. | |
| 6,129,708 A | 10/2000 | Enger | |
| 6,165,187 A | 12/2000 | Reger | |
| 6,217,549 B1 | 4/2001 | Selmon et al. | |
| 6,258,108 B1 | 7/2001 | Lary | |
| 6,270,489 B1 | 8/2001 | Wise et al. | |
| 6,283,947 B1 | 9/2001 | Mirzaee | |
| 6,527,740 B1 | 3/2003 | Jackson et al. | |
| 6,599,267 B1 | 7/2003 | Ray et al. | |
| 6,692,466 B1 | 2/2004 | Chow et al. | |
| 6,695,863 B1 | 2/2004 | Ramzipoor et al. | |
| 6,719,773 B1 | 4/2004 | Boucher et al. | |
| 6,884,257 B1 | 4/2005 | Cox | |
| 7,108,704 B2 | 9/2006 | Trerotola | |
| 7,131,981 B2 | 11/2006 | Appling et al. | |
| 7,279,002 B2 | 10/2007 | Shaw et al. | |
| 7,303,572 B2 | 12/2007 | Melsheimer et al. | |
| 7,517,352 B2 | 4/2009 | Evans et al. | |
| 7,686,824 B2 | 3/2010 | Konstantino et al. | |
| 7,691,086 B2 | 4/2010 | Tkebuchava | |
| 7,708,753 B2 | 5/2010 | Hardert | |
| 7,850,685 B2 | 12/2010 | Kunis et al. | |
| 7,850,710 B2 | 12/2010 | Huss | |
| 7,887,557 B2 | 2/2011 | Kelley et al. | |
| 7,955,350 B2 | 6/2011 | Konstantino et al. | |
| 8,323,307 B2 | 12/2012 | Hardert | |
| 8,328,829 B2 | 12/2012 | Olson | |
| 8,348,987 B2 | 1/2013 | Eaton | |
| 8,366,661 B2 | 2/2013 | Weber et al. | |
| 8,398,662 B2 | 3/2013 | Granada et al. | |
| 8,454,636 B2 | 6/2013 | Konstantino et al. | |
| 8,500,789 B2 | 8/2013 | Wuebbeling et al. | |
| 8,685,049 B2 | 4/2014 | Schur et al. | |
| 8,685,050 B2 | 4/2014 | Schur et al. | |
| 8,702,736 B2 | 4/2014 | Schur et al. | |
| 8,740,849 B1 | 6/2014 | Fischell et al. | |
| 8,870,816 B2 | 10/2014 | Chambers et al. | |
| 9,079,000 B2 | 7/2015 | Hanson et al. | |
| 9,192,747 B2 | 11/2015 | Hardert | |
| 9,282,991 B2 | 3/2016 | Schur et al. | |
| 9,364,255 B2 | 6/2016 | Weber | |
| 9,364,284 B2 | 6/2016 | Groff et al. | |
| 9,510,901 B2 | 12/2016 | Steinke et al. | |
| 9,532,798 B2 | 1/2017 | Schur et al. | |
| 9,592,386 B2 | 3/2017 | Mathur et al. | |
| 9,604,036 B2 | 3/2017 | Burton et al. | |
| 2001/0007059 A1 | 7/2001 | Mirzaee | |
| 2002/0010489 A1 | 1/2002 | Grayzel et al. | |
| 2002/0029052 A1 * | 3/2002 | Evans | A61B 17/22 |
| | | | 606/159 |
| 2002/0143350 A1 | 10/2002 | Heitzmann et al. | |
| 2003/0069547 A1 | 4/2003 | Gonon | |
| 2003/0125756 A1 | 7/2003 | Shturman et al. | |
| 2003/0144677 A1 | 7/2003 | Lary | |
| 2004/0034384 A1 | 2/2004 | Fukaya | |
| 2004/0098014 A1 | 5/2004 | Flugelman et al. | |
| 2004/0122457 A1 | 6/2004 | Weber | |
| 2004/0204738 A1 | 10/2004 | Weber et al. | |
| 2004/0267345 A1 | 12/2004 | Lorenzo et al. | |
| 2005/0055077 A1 | 3/2005 | Marco et al. | |
| 2005/0149102 A1 | 7/2005 | Radisch, Jr. et al. | |
| 2005/0149159 A1 | 7/2005 | Andreas et al. | |
| 2005/0151304 A1 | 7/2005 | Boelens et al. | |
| 2005/0240176 A1 | 10/2005 | Oral et al. | |
| 2006/0089637 A1 | 4/2006 | Werneth et al. | |
| 2006/0111736 A1 | 5/2006 | Kelley | |
| 2006/0116701 A1 | 6/2006 | Crow | |
| 2006/0184191 A1 | 8/2006 | O'Brien | |
| 2007/0005093 A1 | 1/2007 | Cox | |
| 2007/0060863 A1 | 3/2007 | Goeken et al. | |
| 2007/0106215 A1 * | 5/2007 | Olsen | A61B 17/320725 |
| | | | 604/96.01 |
| 2007/0156225 A1 | 7/2007 | George et al. | |
| 2007/0181157 A1 | 8/2007 | Dadourian | |
| 2008/0140051 A1 | 6/2008 | Bei et al. | |
| 2008/0294116 A1 | 11/2008 | Wolter et al. | |
| 2008/0300594 A1 | 12/2008 | Goto | |
| 2008/0300610 A1 | 12/2008 | Chambers | |
| 2009/0099583 A1 | 4/2009 | Butterfield et al. | |
| 2009/0105686 A1 | 4/2009 | Snow et al. | |
| 2009/0192508 A1 | 7/2009 | Laufer et al. | |
| 2009/0204068 A1 | 8/2009 | Nguyen et al. | |
| 2009/0306690 A1 | 12/2009 | Rivers | |
| 2009/0312807 A1 * | 12/2009 | Boudreault | A61B 17/025 |
| | | | 606/86 R |
| 2010/0010521 A1 | 1/2010 | Kurrus | |
| 2010/0121270 A1 * | 5/2010 | Gunday | A61B 17/22012 |
| | | | 604/98.01 |
| 2010/0168737 A1 | 7/2010 | Grunewald | |
| 2010/0168778 A1 | 7/2010 | Braido | |
| 2010/0330147 A1 | 12/2010 | Hossainy et al. | |
| 2011/0060182 A1 | 3/2011 | Kassab et al. | |
| 2011/0152683 A1 * | 6/2011 | Gerrans | A61B 17/22012 |
| | | | 600/435 |
| 2011/0160645 A1 | 6/2011 | Sutermeister et al. | |
| 2011/0184447 A1 | 7/2011 | Leibowitz et al. | |
| 2011/0288479 A1 | 11/2011 | Burton | |
| 2012/0053485 A1 | 3/2012 | Bloom | |
| 2012/0143054 A1 | 6/2012 | Eaton et al. | |
| 2012/0157988 A1 | 6/2012 | Stone et al. | |
| 2012/0172901 A1 | 7/2012 | Manderfeld et al. | |
| 2013/0066346 A1 | 3/2013 | Pigott | |
| 2013/0131594 A1 | 5/2013 | Bonnette et al. | |
| 2013/0150874 A1 | 6/2013 | Kassab | |
| 2013/0237950 A1 | 9/2013 | Gianotti et al. | |
| 2013/0253467 A1 | 9/2013 | Gianotti et al. | |
| 2014/0277002 A1 * | 9/2014 | Grace | A61B 17/22 |
| | | | 606/159 |
| 2014/0364896 A1 | 12/2014 | Consigny | |
| 2015/0133978 A1 | 5/2015 | Paul, Jr. | |
| 2017/0056048 A1 | 3/2017 | Erpen | |
| 2017/0238960 A1 | 8/2017 | Hatta et al. | |

FOREIGN PATENT DOCUMENTS

| | | |
|---|---|---|
| WO | 9502370 A2 | 1/1995 |
| WO | 1996039997 A2 | 12/1996 |
| WO | 9918862 A1 | 4/1999 |
| WO | 02078511 A2 | 10/2002 |

(56) References Cited

FOREIGN PATENT DOCUMENTS

| WO | 02078511 A3 | 10/2002 |
| WO | 2007095125 A2 | 8/2007 |
| WO | 2014106226 A2 | 7/2014 |
| WO | 2014142801 A1 | 9/2014 |
| WO | 2013159066 A1 | 12/2015 |
| WO | 2015190578 A1 | 12/2015 |
| WO | 2015195606 A1 | 12/2015 |
| WO | 2016210167 A1 | 12/2016 |

OTHER PUBLICATIONS

Boston Scientific Corporation, FilterWire EZ, Embolic Protection System for Carotid Arteries, Sep. 2015, http://www.bostonscientific.com/en-US/products/embolic-protection/filterwire-ez-embolic-protection-system.html.
International Search Report, Application No. PCT/US2012/055079, dated Jan. 31, 2013.
Boston Scientific, Rotablator Rotational Atherectomy System, http://www.bostonscientific.com/en-US/products/plaque-modification/rotablator-rotational-atherectomy-system.html, 2017.
Covidien, SpiderFX Embolic Protection Device, 2015, https://www.ev3.net/peripheral/us/embolic-protection/spidertxtrade-embolic-protection-device.htm.
Boston Scientific, Sterling 0.018" Balloon Catheter, Jun. 2015.
Ham, S. et al., Safety of Carbon Dioxide Digital Subtraction Angiography, Archives of Surgery, Dec. 2011.
Alexander, J., CO2 Angiography in Lower Extremity Arterial Disease, Endovascular Today, Sep. 2011, pp. 27-34.

\* cited by examiner

INTRAVASCULAR CATHETER BALLOON DEVICE HAVING A TOOL FOR ATHERECTOMY OR AN INCISING PORTION FOR ATHEROMATOUS PLAQUE SCORING

CROSS REFERENCE TO RELATED APPLICATION

This application claims the benefit of U.S. Provisional Application No. 62/102,755, filed Jan. 13, 2015, the disclosure of which is incorporated herein by reference.

TECHNICAL FIELD

Exemplary embodiments of the present invention relate generally to devices and methods for intravascular catheters. In particular, this invention relates to an improved balloon device with a tool for atherectomy procedures or plaque scoring procedures.

BACKGROUND AND SUMMARY OF THE INVENTION

Atherosclerosis is a chronic condition in which atheromatous plaque accumulates on the inner walls of a blood vessel. As a result, the blood vessel walls can become inflamed and, over time, may harden to form atherosclerotic lesions that cause a narrowing of the vessel lumen. In severe cases, the atherosclerotic lesions can rupture and induce the formation of thrombus (i.e., blood clots), which can prevent blood flow through the narrowed vessel lumen. Atherosclerosis is often the cause of heart attacks, strokes, and peripheral vascular disease.

There are known procedures and devices for treating or otherwise reducing the risks associated with atherosclerosis. For example, an angioplasty is a procedure in which a balloon catheter is inserted into a narrowed region of the vessel lumen via a delivery catheter. The balloon catheter includes a flexible tube having an inflatable balloon at an end thereof. Once positioned in the narrowed region, the balloon is inflated in order to dilate the narrowed vessel lumen. The pressure in the balloon is generally sufficient to compress the accumulated plaque. However, the high pressure of angioplasty balloons required to compress the accumulated plaque can cause damage to the artery walls or surrounding nerves. Restenosis (i.e., re-narrowing of the artery) is also a known risk of angioplasty.

In addition, atheromatous plaque may accumulate over a section of blood vessel that is too long to be treated by a single deployment of an angioplasty balloon. This is particularly common in peripheral artery disease.

Various atherectomy devices are known in the art. For example, directional and rotational devices are known, which remove atheromatous plaque in either a single direction or in all directions surrounding the catheter, respectively. These devices generally operate by the use of a rotating blade. Additionally, atherectomy devices utilizing laser technology are known in the art.

Therefore, it would be desirable to provide an endovascular balloon device with a tool for atherectomy procedures.

In still other cases, it is desirable to fragment the atheromatous plaque accumulation, particularly by a continuous scoring technique. Fragmentation of the atheromatous plaque can provide for more effective angioplasty treatment, alternatively, fragmentation alone may be a sufficient treatment for atherosclerosis. Therefore, it would be desirable to provide an intravascular catheter having an expandable portion that can be selectively controlled by a user.

The present invention relates to an endovascular balloon device having a tool for use during atherectomy or plaque scoring procedures. The present invention is a catheter device. The device contains a catheter tube that can be inserted intravenously into the person's blood vessel. The distal end of the catheter tube contains an inflatable balloon portion. The balloon portion is selectively operable by the user to inflate and deflate between a closed position, wherein the balloon portion has a first diameter, and an opened position, wherein the balloon portion has a second diameter that is larger than the first diameter. The balloon portion is configured to inflate to contact either the atheromatous plaque accumulation or the blood vessel wall, thus providing a stable platform for the attached tool.

The attached tool may be configured to extend beyond the outer diameter of the inflated balloon. In an exemplary embodiment of the present invention, the attached tool is a curved blade configured to excise atheromatous plaque accumulation. In other exemplary embodiments, the attached tool may be a cutting blade configured to incise, fragment, and score the atheromatous plaque accumulation. The blade may be configured to present a cutting surface when the balloon is moved axially. The device may be inserted into a person's vascular system and directed to a zone of attention having atherosclerotic plaque. The balloon portion may be inflated and moved along the length of the atheromatous plaque, thereby performing atherectomy or scoring the plaque depending on which tool is attached. In still other exemplary embodiments, the balloon portion may remain stationary and the cutting surface may remove the atheromatous plaque, such as by a rotational blade, regardless of any motion of the balloon portion.

Any number of different type, size, shape, and styles of attached tools are contemplated for any number of medical procedures. These embodiments, listed only as examples and not intended to be limiting, may include curved or flat surfaces such as scoops and blades, as well as active or passive cutting devices. Active devices may include rotational surfaces that remove atheromatous plaque by their own motion, not necessarily by the motion of the balloon platform. Passive devices may include surfaces that remove atheromatous plaque only by the motion of the balloon platform advancing, retracting, or rotating within the blood vessel. A combination of active and passive devices may be utilized as well. Further, passive devices may be utilized which score and fragment, rather than remove, the atheromatous plaque.

Various aspects of this invention will become apparent to those skilled in the art from the following detailed description of the preferred embodiments, when read in light of the accompanying drawings.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Figure 1:
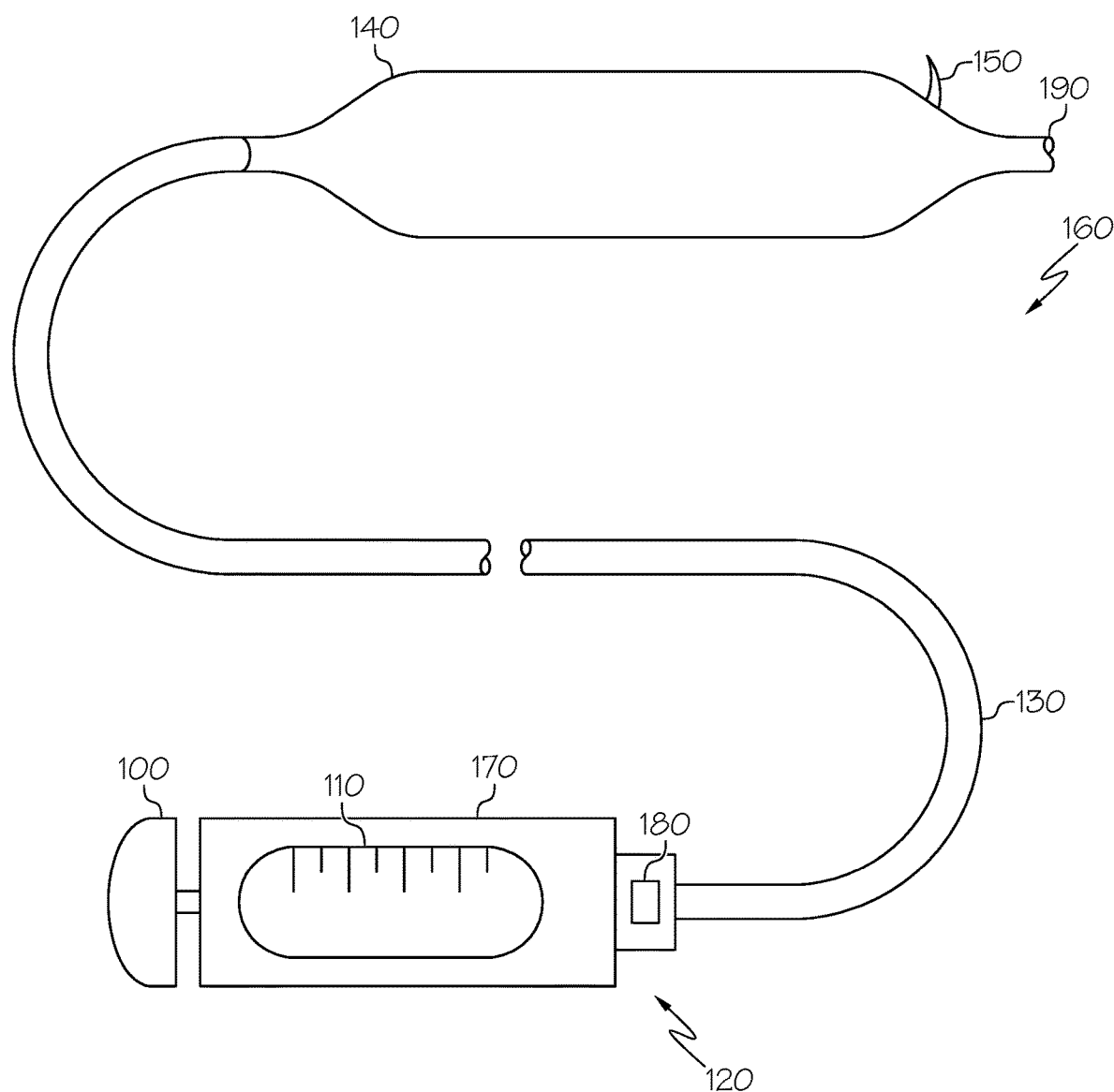
FIG. 1 is a plan view of the device.

Referring now to the drawings, there is illustrated in FIG. 1 a catheter device, indicated generally at 160, in accordance with the present invention. The illustrated catheter device 160 is configured to treat or reduce the risks associated with atherosclerosis. In general, the catheter device 160 contains an inflatable balloon 140 with a tool 150. In exemplary embodiments of the present invention, the tool 150 is configured to incise, fragment, and score atheromatous plaque. In other exemplary embodiments of the present invention, the tool 150 may be configured to remove atheromatous plaque (i.e. perform atherectomy). The tool 150 may be any cutting surface configured to provide an incision when the balloon is moved axially. These examples are merely exemplary and are not intended to be limiting. Any type of tool 150 for any type of medical procedure is contemplated.

The catheter device 160 comprises a handle assembly, indicated generally at 120. The handle assembly 120 comprises an inflation device 100, such as a plunger or other suitable device for inflating the balloon 140. The handle assembly 120 further comprises a valve 180 that can be selectively operated to permit fluid to flow only in one direction, both directions, or in neither direction. When inflating the balloon 140, the user may operate the valve 180 in such a way to ensure that fluid may only pass into the balloon 140. The user may then close the valve 180 such that fluid may not pass in either direction. Similarly, when deflating the balloon, the user may operate the valve 180 in such a way to ensure that fluid may only leave the balloon 140, or alternatively, to allow fluid to pass in either direction.

It should be considered that the use of plunger and the valve 180 are merely exemplary. Those skilled in the art will recognize that there are a number of known ways by which the inflation and deflation of the balloon 140 may be accomplished. In an exemplary embodiment, the valve 180 may not be required. The balloon 140 may be comprised of any sufficiently biocompatible and flexible material including, but not limited to, polymers, rubber compounds, silicone, latex, polyvinyl chloride, some combination thereof, or the like.

The handle assembly 120 may further comprise a measuring device 110, located on or within a housing 170. The housing 170 may surround the inflation/deflation mechanism as well as the measuring device 110. The measuring device 110 may indicate status information about the balloon 140. The status information may include, but is not limited to, the pressure and location of the balloon 140 and the location and operational status of the tool 150. This list is merely exemplary, skilled artisans will appreciate that other information may be displayed. In the illustrated embodiment, the measuring device 110 comprises graduated marks. In other exemplary embodiments, the measuring device 110 may take the form of numbers or other markings. In still other exemplary embodiments, the measuring device 110 may take the form of an analog or digital display. The handle assembly 120 may be comprised of any sufficiently rigid material such as polymer, steel, or the like.

The handle portion 120 is connected to and in communication with the balloon device via a catheter tube 130. The catheter tube 130 may comprise an inner lumen that facilitates the flow of a fluid from the inflation device 100 to the balloon 140 to inflate and deflate the balloon 140. Said fluid may be air. Skilled artisans will appreciate that other fluids that facilitate the inflation of the balloon 140 may be utilized with the present invention. The catheter tube 130 may be made of any biocompatible and sufficiently flexible material such as a polymer or the like. The catheter tube 130 may also contain linkage, such as by wire, for the flow of information between the balloon 140 and tool 150 to the measuring device 110. Said linkage may be configured to provide communication and physical manipulation between the handle assembly 120 and the attached tool 150. Additionally, the catheter tube 130 is configured to provide a physical connection and control between the handle assembly 120 and the balloon 140 such that the user may manipulate the balloon 140 axially by extending or retracting the handle 120. In other embodiments of the present invention the catheter tube 130 may be made of sufficiently stiff material such that the user may further manipulate the balloon 140 rotationally by twisting the handle 120. In still other embodiments, the user may be able to manipulate the balloon 140 rotationally by way of electronic or physical control of linkage running from handle 120 to balloon 140. The catheter tube 130 may be connected to the handle assembly 120 and the balloon 140, respectively, by means of a threaded fastener, press fit, clamp, adhesive, or other attaching means.

The catheter tube 130 may be further configured to slide atop a guide wire (not shown) that is inserted and manipulated to a treatment site prior to insertion of the present invention. The catheter tube 130 and balloon 140 may be configured such that they may slide atop a guide wire while maintaining a watertight engagement to facilitate inflation and deflation of the balloon 140, even when the guide wire extends through and beyond the termination of the balloon. The balloon may terminate at an end cap 190. The end cap 190 may be configured to permit the guide wire to pass therethrough while maintaining a seal.

Figure 2:
FIG. 2 is an enlarged side view of the distal portion of the device of FIG. 1.

Referring now to FIG. 2, the tool 150 may comprise an atherectomy tool. In the present embodiment the tool 150 is in the shape of a curved blade, configured to remove atheromatous plaque from a blood vessel wall. The tool 150 may be configured to provide a cutting surface when the balloon moves in an axial direction. The atherectomy tool 150 may be configured to extend above the outer diameter of balloon 140, permitting the atherectomy tool 150 to contact and remove atheromatous plaque from a blood vessel wall. In other exemplary embodiments, the atherectomy tool 150 may not extend beyond the outer surface of the balloon 140. The atherectomy tool 150 may be comprised of any biocompatible and sufficiently rigid and strong material such as a polymer, rubber compound, silicone, latex, polyvinyl chloride, steel, steel alloy, a combination thereof, or the like.

Figure 3:
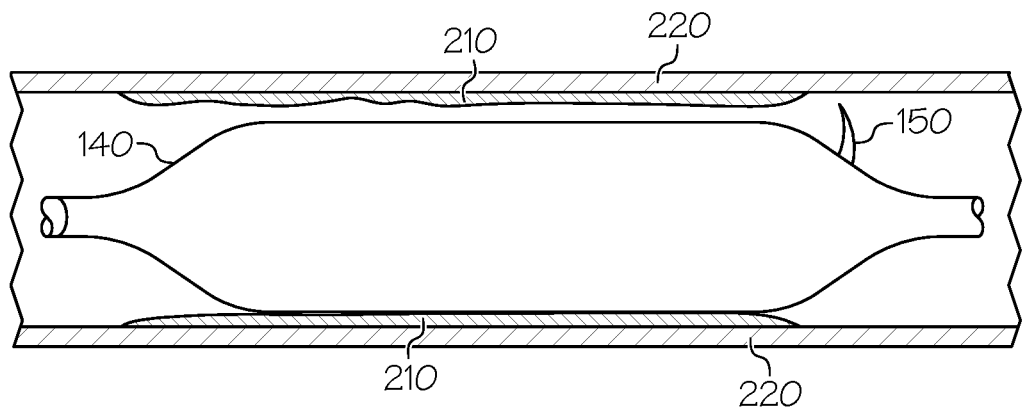
FIG. 3 is a side view of the device of FIG. 2 as located in a cross section of a blood vessel with atheromatous plaque accumulation.

FIG. 3 illustrates the balloon 140 located in a blood vessel 220 having atheromatous plaque accumulation 210. The balloon 140 may be placed in a deflated position. This may likewise place the tool 150 in a retracted position. After inserting the optional guide wire, the device 160 may be mounted thereon. In other exemplary embodiments, no guide wire is used and the device 160 is directly inserted into the person's vascular system. Regardless, the balloon 140 is then maneuvered to a zone of attention within the person's vascular system. In exemplary embodiments, the zone of attention is a region of atheromatous plaque accumulation 210. The user may manipulate the balloon 140 via handle assembly 120 and catheter tube 130. The user may then activate the inflation mechanism 100 and the balloon 140 may be inflated. This may involve manipulation of the valve 180. In exemplary embodiments, the outer diameter of the balloon 140 may be expanded until it contacts the atheromatous plaque accumulation 210, this may place the tool 150 in an extended position for treatment. It should be appreciated, however, that in other embodiments the balloon 140 may be located and inflated to contact the blood vessel walls 220.

Once the balloon 140 is inflated, the device 160 may be manipulated, such as but not limited to by pulling on the handle assembly 120, along the zone of attention. The balloon 140 and attached tool 150 thereby contact and remove the atheromatous plaque accumulation 210, performing atherectomy. In other exemplary embodiments, the tool 150 may contact the blood vessel wall or other tissue. Any type of medical treatment is contemplated. The balloon 140 may then be deflated, thereby placing the tool 150 in the retracted position. The process may be repeated as desired at this or another zone of attention. Alternatively, the device 160 may be immediately removed from the person.

It should be appreciated, however, that the tool 150 may be any kind of tool. This may include, but is not limited to, atherectomy devices, needles and other drug delivery devices, incising and scoring elements, heating and cooling elements such as cauterizing devices, diagnostic devices such as biopsy tools, and imaging devices such as radiological imaging devices, and therapeutic devices such as targeted radiation treatments. It should further be appreciated that any medical treatment may be performed using the device 160. It should be further appreciated that the user may perform steps appropriate for the proper use of the other attached tools and other treatments.

Figure 4:
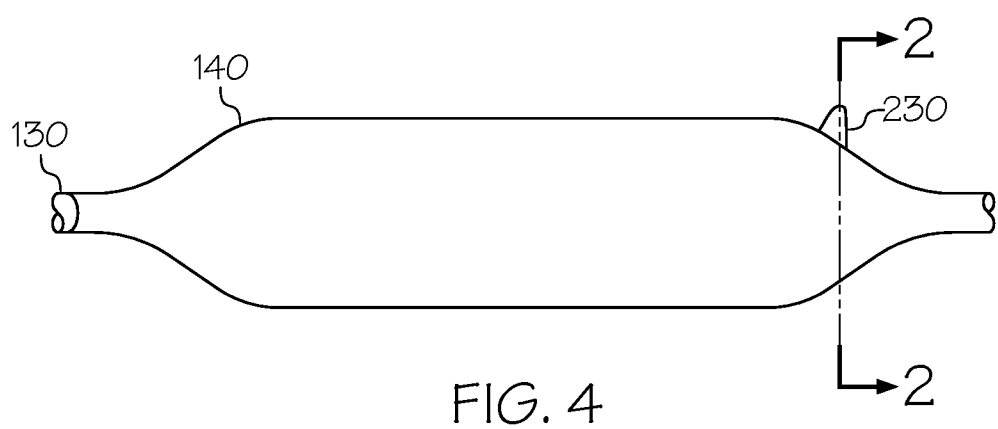
FIG. 4 is a side view of another exemplary embodiment of the device of FIG. 2.

Referring now to FIG. 4, the tool may comprise a burr 230 configured to scrape and remove atheromatous plaque accumulation. The burr 230 may be rounded and be of various shapes. The burr 230 may contain a roughened surface for abrasion. The abrasive surface portion of the burr 230 may extend over part or all of tool 230. The burr 230 may be comprised of a coating of abrasive material such as diamonds, steel, polymer, or other suitably abrasive and biocompatible materials and surfaces. The burr 230 may be configured to only present a roughened surface when the balloon is moved in an axial direction.

Figure 5:
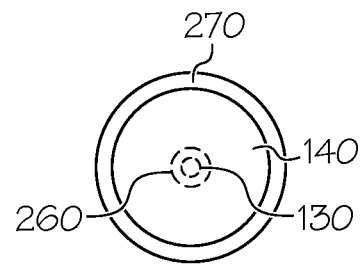
FIG. 5 is a sectional view of another exemplary embodiment of the device of FIG. 2 and FIG. 4 taken along section lines 1-1 and 2-2, respectively.

Referring now to FIG. 5, a cross section of an exemplary embodiment of the device illustrated in FIG. 2 and FIG. 4 is shown. The cross section, taken along section line 1-1 of FIG. 2 or 2-2 of FIG. 4, respectively, illustrates the balloon 140 concentric with a circumferential tool 270. In the illustrated embodiment, the circumferential tool 270 surrounds the entirety of the balloon 140. The circumferential tool 270 may be configured to only present a cutting surface when the balloon is moved axially. The outer circumference of the circumferential tool 270 may be arcuate and configured to match the outer surface of the balloon 140. In other embodiments, the circumferential tool 270 may be defined by a flat upper edge. The inner circumference of the circumferential tool 270 may be arcuate and configured to attach flush to the outer surface of the balloon 140 though it is contemplated that the circumferential tool 270 may be attached at to any point of the outer surface of the balloon 140. It should be considered that the outer circumferences of the circumferential tool 270 may extend any distance beyond the outer surface of the balloon 140. In other exemplary embodiments, the circumferential tool 270 may not extend beyond the outer surface of the balloon 140.

Figure 6:
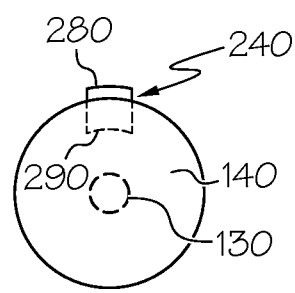
FIG. 6 is a sectional view of another exemplary embodiment of the device of FIG. 2 and FIG. 4 taken along section line 1-1 and 2-2, respectively.

Referring now to FIG. 6 there is illustrated a section view of another exemplary embodiment of the devices illustrated in FIG. 2 and FIG. 4. The cross section, taken along section line 1-1 of FIG. 2 or 2-2 of FIG. 4, respectively, illustrates the balloon 140 concentric with a medical device, indicated generally at 240. In the illustrated embodiment, the medical device 240 surrounds only a portion of the outer surface of the balloon 140. The medical device 240 may be a blade that is configured to only present a cutting surface when the balloon is moved axially.

The outer circumference of the medical device 240 may be defined by an arcuate surface 280 and the inner circumference of the medical device 240 may be defined by an arcuate surface 290. In other exemplary embodiments, the medical device 240 may be defined by flat upper and lower edges. The catheter tube 130 is indicated by hidden lines where it attaches to an end of the balloon 140. It should be considered that the outer circumference 280 of the medical device 240 may be located at any distance beyond the outer surface of the balloon 140. In other exemplary embodiments, the medical device 240 may not extend beyond the outer surface of the balloon 140. Similarly, it should be considered that the inner circumference 290 of the medical device 240 may be located at any distance beyond the outer circumference of the catheter tube 130 but not beyond the outer diameter of the balloon 140. It should also be considered that the medical device 240 may extend to surround any portion of the total outer surface of balloon 140. Further, it should be considered that the multiple sections of medical device 240 may be utilized to cover any portion of the outer surface of the balloon 140.

Figure 7:
FIG. 7 is a side view of another exemplary embodiment of the device of FIG. 2.

Referring now to FIG. 7, another exemplary embodiment of the present invention is illustrated. In the present embodiment, the balloon 140 is attached to catheter tube 130. The balloon 140 may be comprised of a plurality of incising devices 300, 310, and 320 (a fourth tool on the opposite surface of the balloon from tool 310 is not shown) that are attached to the outer surface of the balloon. The incising devices 300, 310, and 320 may extend outwardly in a radial direction from the outer surface of the balloon and extend in parallel with a longitudinal axis of the balloon. In this way, the incising elements 300, 310, and 320 may be configured to provide an incision when the balloon 140 is moved in an axial direction. Although four incising devices are illustrated, this is merely exemplary and not intended to be limiting, any number of incising devices are contemplated. The incising devices 300, 310, and 320 may be thin blades extending radially outward to facilitate the scoring and fragmentation of the atheromatous plaque accumulation.

The balloon 140 may be deflated and inserted into the person intravenously. Alternatively, the positioning of the balloon 140 may be accomplished by inserting balloon 140 atop a guide wire (not pictured) and manipulating the balloon 140 along the guide wire to a treatment site. Once positioned by the surgeon, the balloon 140 may be inflated such that the incising devices 300, 310, and 320 contact the atheromatous plaque accumulation, blood vessel wall, or other tissue. The balloon 140 and attached incising devices 300, 310, and 320 may then by retracted by the user such that the incising devices 300, 310, and 320 score and fragment the atheromatous plaque accumulation or otherwise treat the area. The balloon 140 may then be deflated and removed from the person. The above steps may be repeated as appropriate to achieve a desirable amount of scoring and fragmentation or other treatment effect.

Figure 8:
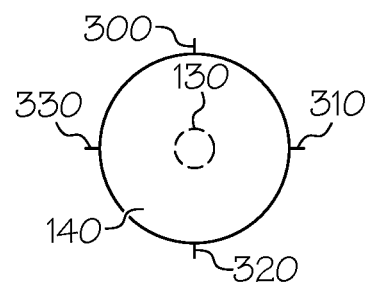
FIG. 8 is a sectional view of the device of FIG. 7 taken along section line 3-3.

Referring now to FIG. 8, a sectional view taken along section line 3-3 of FIG. 7. The balloon 140 is attached to catheter tube 130. The incising devices 300, 310, and 320 are spaced evenly across the surface of the balloon 140. It should be considered that while the illustrated embodiment is shown with four incising tools 300, 310, 320, and 330, any number of incising tools may be utilized. It should further be considered, that while the illustrated embodiment shows the incising tools evenly spaced across the outer surface of the balloon 140, the incising tools could be located in any configuration on the outer surface of balloon 140.

Figure 9:
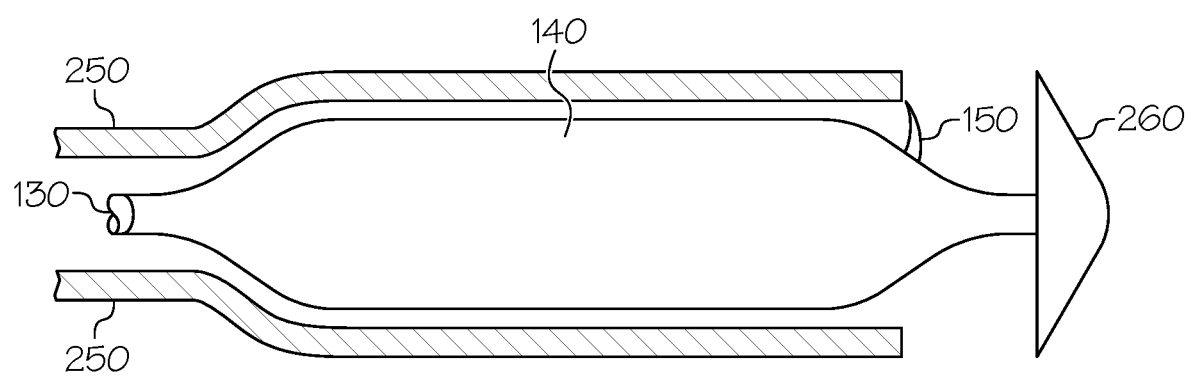
FIG. 9 is a sectional view of the device of FIG. 2.

FIG. 9 illustrates a sectional view of the device 160 of FIG. 2 with the balloon 140 in a deflated position. In this exemplary embodiment, the device 160 may further comprise a sheath 250. The sheath may extend over the balloon 140 and the attached tool 150. It is contemplated, however, that the sheath 250 may be used with any of the embodiments of the present invention, including but not limited to, in conjunction with the burr 230, the circumferential tool 270, the medical device 240, and the incising devices 300, 310, and 320. The balloon 140 may fit snugly into the sheath such that it forms a substantially watertight engagement therebetween. A drug coating may be placed on the outer surface of the balloon 140 to aid in treatment. The medication in the drug coating may be activated upon removal of the sheath 250 and the subsequent exposure to the blood vessel fluids. A lubricious coating may be placed between the outer surface of the balloon 140 and the inner surface of the sheath 250 to aid in the movement of the sheath 250 relative to the balloon 140. The lubricious coating, when used in conjunction with the drug coating, may prevent the drug coating from being disturbed when the sheath 250 is moved relative to the balloon 140.

In other exemplary embodiments, the sheath 250 may be used in conjunction with a tapered insertion tip 260. The tip 260 may form a watertight engagement with the sheath 250 when abutted to the sheath 250. When the balloon 140 is inflated, the outer surface of the balloon 140 and any attachments may extend beyond the tip 260.

The sheath 250 may be attached to the catheter tube 130 and operated by an internal mechanism that is in communication with the handle assembly 120. This may include a mechanical linkage that extends through the lumen created by the catheter tube 130, electrical wires, or the like. In exemplary embodiments of the present invention, the inflation of the balloon 140 may exert a force on the sheath 250, which causes the sheath 250 to be moved to a retracted position. The sheath 250 may be biased in the extended position such that upon deflation of the balloon 140, the sheath 250 may move back into the extended position. In other exemplary embodiments of the present invention, the sheath 250 may be affixed to an outer member (not shown) that is disposed about the catheter tube 130. The outer member may extend to the handle assembly 120 and may be moved axially to extend or retract the sheath 250.

In an exemplary embodiment of the present invention, the sheath 250 may be placed in an extended position over the balloon 140 when the balloon 140 is in a deflated state and before the device 160 is inserted into the patient's vascular system. The sheath 250 may be retracted once the balloon 140 has traveled to the treatment site. The sheath 250 may be replaced once the balloon is returned to the deflated state.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

What is claimed is:

1. An intravascular device for medical treatment of a zone of attention within an individual's vascular system, said zone of attention comprising a blood vessel and atherosclerotic material, said device comprising:
   a balloon configured to move between an inflated position and a deflated position;
   a blade secured to a downward sloping portion of an outer surface of the balloon, said blade comprising an upper, sharpened edge adapted to present a cutting surface when the balloon is placed in the inflated position and moved in an axial direction, wherein said sharpened edge extends laterally transverse to a longitudinal axis of the balloon and is adapted to remove plaque when the device is moved axially through the blood vessel;
   a handle;
   an elongated tube having a distal end affixed to the balloon and having a proximal end affixed to the handle, said elongated tube defining an inner channel for the passage of an inflation fluid;
   a pump secured to the handle and configured to pressurize the inflation fluid, wherein said pump is in fluid communication with the balloon via the inner channel;
   a coating comprising a therapeutic agent and a lubricious agent, said coating located about substantially the entire outer surface of the balloon;
   a sheath configured to be moved between a closed position where the sheath is disposed about the entire balloon and the entire blade, and an opened position where the entire blade and the entire balloon is exposed; and
   a tip member located at a distal end of the balloon and configured to provide a watertight engagement between said sheath and said tip member such that the coating is protected from exposure to fluids within the blood vessel when the tip member is abutted to said sheath.

2. The device of claim 1 wherein:
the balloon is configured to inflate to a maximum outer diameter; and
the sharpened edge of the blade is sized to extend beyond the maximum outer diameter of the balloon when the balloon is placed in the inflated position.

3. A method for the treatment of a zone of attention within an individual's vascular system, said zone of attention comprising a blood vessel and atherosclerotic material in a person comprising the steps of:
providing an intravascular balloon device comprising:
a balloon comprising a blade defining an upper, sharpened edge oriented laterally perpendicular to a longitudinal axis of the balloon so as to present a cutting surface when the balloon is moved axially, a catheter tube extending from an end of said balloon, wherein the blade is located on a downward sloping portion of the balloon;
a handle assembly affixed to a distal end of the catheter tube relative to the balloon and where said handle assembly comprises an inflation device;
a coating comprising a therapeutic agent and a lubricious agent, said coating located about substantially an entire outer surface of the balloon;
a sheath configured for movement between a closed position and an opened position; and
a tip member located at a distal end of the balloon;
wherein said inflation device is in fluid communication with said balloon by way of said catheter tube;
placing the balloon in a deflated state;
placing the sheath in the closed position such that the sheath is disposed about the entire balloon and the entire blade and abuts the tip member to create a watertight engagement between said sheath and said tip member such that the coating is protected from exposure to fluids within the blood vessel;
introducing the balloon into the person's vascular system while maintaining the sheath in the closed position;
manipulating the balloon to the intravascular zone of attention while maintaining the sheath in the closed position;
placing the sheath in the opened position such that the coating is exposed;
inflating the balloon to an inflated state such that the outer surface of the balloon contacts the atherosclerotic material and the blade extends at least partially within said atherosclerotic material;
manipulating the inflated balloon along the zone of attention while the balloon is maintained in the inflated state so as to remove atherosclerotic material located therein and release the therapeutic agent along the zone of attention;
placing the balloon in the deflated state; and
removing the balloon from the person.

4. The method of claim 3 further comprising the steps of:
providing a guide wire configured to permit the intravascular balloon device to slide atop;
introducing the guide wire into the person's vascular system; and
manipulating the guide wire to the intravascular zone of attention.

5. The device of claim 3 wherein:
the balloon is configured to inflate to a maximum outer diameter; and
the sharpened edge of the blade is sized to extend beyond the maximum outer diameter of the balloon when the balloon is inflated.

* * * * *